(12) United States Patent
Maurice et al.

(10) Patent No.: US 7,655,394 B2
(45) Date of Patent: Feb. 2, 2010

(54) HEPATITIS C VIRUS NS2/3 ACTIVITY ASSAY

(75) Inventors: Roger Maurice, Montreal (CA); Diane Thibeault, Laval (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 11/553,531

(22) Filed: Oct. 27, 2006

(65) Prior Publication Data
US 2007/0212754 A1    Sep. 13, 2007

Related U.S. Application Data

(60) Provisional application No. 60/730,999, filed on Oct. 28, 2005.

(51) Int. Cl.
*C12Q 1/00* (2006.01)
(52) U.S. Cl. .................................................. 435/4
(58) Field of Classification Search ........................ None
See application file for complete search history.

(56) References Cited

U.S. PATENT DOCUMENTS

| 5,739,002 | A | 4/1998 | DeFrancesco et al. |
| 6,251,583 | B1 | 6/2001 | Zhang et al. |
| 6,815,159 | B2 | 11/2004 | Thibeault et al. |
| 2002/0177725 | A1* | 11/2002 | Priestley .................... 558/288 |
| 2002/0192640 | A1* | 12/2002 | Thibeault et al. .............. 435/5 |

FOREIGN PATENT DOCUMENTS

| JP | 11124400 | * | 7/1999 |
| WO | WO 97/08304 | * | 3/1997 |
| WO | WO 01/68818 A2 | | 9/2001 |
| WO | WO 02/16379 A1 | | 2/2002 |
| WO | WO 02/48375 A2 | | 6/2002 |

OTHER PUBLICATIONS

Welbourn et al., Hepatitis C Virus NS2/3 Processing is Required for NS3 Stability and Viral RNA Replication, Journal of Biological Chemistry Papers in Press, Jun. 24, 2005, Manuscript M505019200.*
"IUPAC-IUB Commission on Biochemical Nomenclature Symbols for Amino-Acid Derivatives and Peptides Recommendations (1971)"; Biochemistry, vol. 11, No. 9, p. 1726, 1972.
A. A. Kolykhalov, et al. "Hepatitis C Virus-Encoded Enzymatic Activities and Conserved RNA Elements in the 3' Nontranslated Region are Essential for Virus Replication in Vivo", J. of Virology, vol. 74, No. 4, p. 2046-2051, 2000.
D. Thibeault, et al. "In Vitro Characterization of a Purified NS2/3 Protease Variant of Hepatitis C Virus", J. of Biological Chemistry, vol. 276, No. 49, p. 46678-46684, 2001.
M. Pallaoro, et al. "Characterization of the Hepatitis C Virus NS2/3 Processing Reaction by Using a Purified Precursor Protein", J. of Virology, vol. 75, No. 20, p. 9939-9946, 2001.
E. Bianchi, et al., "Synthetic Depsipeptide Substrates for the Assay of Human Hepatitis C Virus Protease", Analytical Biochemistry, vol. 237, p. 239-244, 1996.

S. R. LaPlante, et al., "Solution Structure of Subtrate-based Ligands when Bound to Hepatitis C Virus NS3 Protease Domain", J. of Biological Chemistry, vol. 274, No. 26, p. 18618-18624, 1999.
P.L. Darke, et al., "Inhibition of Hepatitis C Virus NS2/3 Processing by NS4A Peptides", J. Biological Chemistry, vol. 274, No. 49, p. 34511-34514, 1999.
C. Lin, et al., "A Central Region in the Hepatitis C Virus NS4A Protein Allows Formation of an Active NS3-NS4A Serine Proteinase Complex In Vivo and In Vitro", J. of Virology, vol. 69, No. 7, p. 4373-4380, 1995.
A. Urbani, et al., "Multiple Determinants Influence Complex Formation of the Hepatitis C Virus NS3 Protease Domain with Its NS4A Cofactor Peptide", Biochemistry, vol. 38, p. 5206-5215, 1999.
D. S. Waugh, "Making the Most of Affinity Tags", Trends in Biotechnology, vol. 23, No. 6, p. 316-320, 2005.
C. Steinkuhler, et al., "Activity of Purified Hepatitis C Virus Protease NS3 on Peptide Substrates", J. of Virology, vol. 70, No. 10, p. 6694-6700, 1996.
J-H. Zhang, et al., "A Simple Statistical Parameter for Use in Evaluation and Validation of High Throughput Screening Assays", J. of Biomolecular Screening, vol. 4, No. 2, p. 67, 1999.
J.C. Ferreon, et al., "Molecular Determinants of TRIF Proteolysis Mediated by the Hepatitis C Virus NS3/4A Protease", J. Biological Chemistry, vol. 280, No. 21, pp. 20483-20492, 2005.
J.O. Koch, et al., "In Vitro Studies on the Activation of the Hepatitis C Virus NS3 Proteinase by the NS4A Cofactor", Virology, vol. 221, p. 54-66, 1996.
L. Pieroni, et al., "In Vitro Study of the NS2-3 Protease of Hepatitis C Virus", J. of Virology, vol. 71, No. 9, p. 6373-6380, 1997.
M. M. Martin, et al., "Single-Cell Resolution Imaging of Membrane-Anchored Hepatitis C Virus NS3/4A Protease Activity", Biological Chemistry, vol. 387, p. 1075, 2006.
A. Berger, et al., "Mapping the Active Site of Papain with the Aid of Peptide Substrates and Inhibitors", Phil. Trans. Roy. Soc. London, B257, p. 249-264, 1970.

* cited by examiner

*Primary Examiner*—Gary B Nickol
*Assistant Examiner*—Nicole Kinsey White
(74) *Attorney, Agent, or Firm*—Michael P. Morris; Mary-Ellen M. Devlin; David A. Dow (57) ABSTRACT

The invention provides a novel assay for NS2/3 cleavage detection, particularly, a novel assay for the detection of the NS3 cleavage product in the presence of uncleaved NS2/3 based on discrimination of the activity of the resulting NS3 protease product from the NS3 protease activity of the NS2/3 uncleaved protein. Certain reaction conditions allow this discrimination in situ without having to resort to physical separation of both proteases by decreasing the NS3 protease activity of the NS2/3 protein and increasing the NS3 protease activity of the resulting NS3 protease product, thereby producing a "signal window" upon which it is feasible to distinguish and measure NS3 protease activity produced from the cleavage of NS2/3.

14 Claims, 2 Drawing Sheets

NS2/3 Protease Assay Based on NS3 Protease Activity
Z' Determination

+ Control (n=43)
34077 ± 1807 FU
CV=5.3%

- Control (n=51)
15585 ± 954 FU
CV=6.1%

NS2/3 Protease Assay Based on NS3 Protease Activity
$IC_{50}$ curve

HEPATITIS C VIRUS NS2/3 ACTIVITY ASSAY

This application claims benefit from U.S. Provisional Application 60/730,999 filed Oct. 28, 2005, the contents of which are incorporated herein.

FIELD OF THE INVENTION

The present invention relates to an assay for detecting cleavage of HCV protein in a sample, and more particularly, to an assay for the selective detection of HCV NS2/3 auto-cleavage activity, and even more particularly to the identification of potential HCV inhibitor compounds.

BACKGROUND OF THE INVENTION

Hepatitis C virus (HCV) is the major etiological agent of post-transfusion and community-acquired non-A non-B hepatitis worldwide. A high percentage of carriers become chronically infected and many progress to chronic liver disease, so called chronic hepatitis C. This group is in turn at high risk for serious liver disease such as liver cirrhosis, hepatocellular carcinoma and terminal liver disease leading to death.

HCV is an enveloped positive strand RNA virus in the Flaviviridae family. The single strand HCV RNA genome is of positive polarity and comprises one open reading frame (ORF) of approximately 9600 nucleotides in length, which encodes a linear polyprotein of approx. 3010 amino acids. In infected cells, this polyprotein is cleaved at multiple sites by cellular and viral proteases to produce structural and non-structural (NS) proteins. The structural proteins (C, E1, E2 and p7) comprise polypeptides that constitute the virus particle. Processing of the structural proteins is catalyzed by host cell proteases. The non-structural proteins (NS2, NS3, NS4A, NS4B, NS5A, NS5B) encode for enzymes or accessory factors that catalyze and regulate the replication of the HCV RNA genome. The generation of the mature non-structural proteins is catalyzed by two virally encoded proteases. The first is the NS2/3 protease which auto-catalyses the cleavage between NS2 and NS3. The NS3 contains a N-terminal serine protease domain and catalyzes the remaining cleavages from the polyprotein. The released NS4A protein has at least two roles. The first role is forming a stable complex with NS3 protein and assisting in the membrane localization of the NS3/NS4A complex; the second is acting as a cofactor for NS3 protease activity. This membrane-associated complex, in turn catalyzes the cleavage of the remaining sites on the polyprotein, thus effecting the release of NS4B, NS5A and NS5B.

The cleavage of the Hepatitis C Virus (HCV) polyprotein between the nonstructural proteins NS2 and NS3 is mediated by the NS2/3 protease, a protease activity that is encoded by the NS2 region and the minimal NS3 protease domain which flank the cleavage site. NS2/3 protease is expressed in virally infected hepatocytes and experimental data are consistent with its essential role in viral propagation and disease. Indeed, no productive infection was observed in chimpanzees upon inoculation of HCV clones containing mutations abolishing NS2/3 protease activity, suggesting that this HCV-encoded enzyme is essential for productive replication in vivo (1).

A minimal catalytic region of NS2/3 protease has been defined and includes the C-terminus of NS2 and the N-terminal NS3 protease domain (2-5). The NS2/3 (904-1206) variant from HCV genotype 1b was purified from *E. coli* inclusion bodies and refolded by gel filtration chromatography as previously described (2, 3). The purified inactive form of NS2/3 (904-1206) can be activated by the addition of glycerol and detergent to induce autocleavage at the predicted site between the residues leucine 1026 and alanine 1027 (2, 3). In vitro, the isolated form of NS2/3 protein possesses both protease activities i.e. the NS2/3 protease auto-cleavage activity and the NS3 protease activity. Separation of the products resulting from the cleavage of the NS2/3 precursor, or at least discrimination between the two forms of NS3 protease activity is required to assess the amount of NS3 protease produced by auto-cleavage of NS2/3 in the same reaction mixture.

NS2/3 protease cleavage detection assays based on the separation of the NS2 and NS3 products from the NS2/3 precursor by SDS-PAGE and by HPLC have been reported, as well as an assay based on the NS3 protease activity of the NS2/3 protein which also requires separation of the NS2/3 uncleaved precursor from the NS3 protease product (2-5). Such methods can be time-consuming and are not adapted for rapid screening. Moreover, no assay has yet been developed having the selectivity to detect NS2/3 cleavage products in the presence of uncleaved NS2/3.

It would, thus, be desirable to develop an efficient NS2/3 cleavage assay which overcomes one or more disadvantages of existing assays. Particularly, it is desirable to develop an efficient NS2/3 cleavage assay which discriminates between the NS3 protease activities of the NS2/3 protein and the NS3 protease cleavage product.

A novel NS3-selective assay method is provided comprising cleavage of NS2/3 protease in a sample and treatment of the cleaved sample which enables detection of cleavage product NS3 therein. The method is useful to detect NS3 cleavage product without having to separate NS2/3 precursor therefrom.

SUMMARY OF THE INVENTION

The present invention provides a novel assay for NS2/3 cleavage detection. More particularly, the present invention provides a novel assay for the detection of the NS3 cleavage product in the presence of uncleaved NS2/3 based on discrimination of the activity of the resulting NS3 protease product from the NS3 protease activity of the NS2/3 uncleaved protein.

We have found that certain reaction conditions allow this discrimination in situ without having to resort to physical separation of both proteases. These conditions allow this discrimination by decreasing the NS3 protease activity of the NS2/3 protein and increasing the NS3 protease activity of the resulting NS3 protease product, thereby producing a "signal window" upon which it is feasible to distinguish and measure NS3 protease activity produced from the cleavage of NS2/3.

In the present invention, following self-cleavage of NS2/3 to generate an NS3 product, the sample is incubated with an NS3-substrate in the presence of a sufficient amount of NS4A cofactor and a suitable detergent. Such suitable conditions will produce a discriminating effect between both forms of the protease.

Therefore, in a first aspect of the present invention, there is provided a method of detecting NS2/3 autocleavage activity in a sample containing NS2/3 protease, the method comprising the steps of:

a) subjecting the sample to conditions under which at least a portion of the NS2/3 protease is self-cleaved to yield a NS3 protease product;

b) incubating the sample containing the NS3 protease product generated in step a) with a suitable amount of a NS4A cofactor in the presence of suitable detergent and an appropriate NS3-substrate under conditions sufficient to permit the NS3 protease product to catalyze cleavage of the NS3-substrate to produce an NS3-substrate byproduct thereof; and c) detecting the NS3-substrate byproduct generated in step b), whereby the detection of NS3-substrate byproduct indicates NS2/3 autocleavage activity in the sample.

As will be well understood by a person of skill in the art, the detection of NS3-substrate byproduct may be measured to yield a specific amount correlating with the amount of NS2/3 autocleavage.

The present invention is also useful to screen candidate NS2/3 inhibitor compounds that may be useful as anti-HCV therapeutics.

Therefore, in a second aspect of the present invention, there is provided an assay for screening a candidate compound for NS2/3 autocleavage inhibitory activity in a sample containing NS2/3 protease, the assay comprising:

a) subjecting a first sample comprising NS2/3 protease, to conditions under which at least a portion of NS2/3 protease is self-cleaved to yield a NS3 protease product;

b) subjecting a second sample comprising NS2/3 protease, in the presence of a candidate compound to the same conditions as those in step a);

c) incubating each of the first and second samples with a sufficient amount of a NS4A cofactor, in the presence of a suitable detergent and an appropriate NS3-substrate for a period of time sufficient to permit the NS3 protease product to catalyze cleavage of the NS3-substrate, thereby generating an NS3-substrate byproduct;

d) determining the amount of NS3-substrate byproduct generated in each of the first and second samples, whereby a decrease in amount of NS3-substrate byproduct generated in the second sample as compared with the amount of NS3-substrate byproduct generated in the first sample indicates that the candidate compound may be an inhibitor of NS2/3 autocleavage activity.

As will be recognized by persons of skill in the art, other types of auto-cleaving proteases similar or homologous to the HCV NS2/3 protease may be used in the method/assay of the present invention in the search for respective inhibitors. Such other proteases may be found in pestiviruses such as, but not limited to: GB virus A, B, or C; bovine viral diarrhea virus (BVDV); Classical Swine Fever virus; Border disease virus; bovine pestivirus; and porcine pestivirus.

These and other aspects of the present invention are described herein by reference to the following figures.

DETAILED DESCRIPTION OF THE PRESENT INVENTION

Definitions

Unless otherwise defined, all technical and scientific terms used herein have the same meaning as those commonly understood by one of ordinary skill in the art to which the invention pertains. Generally, the procedures for cell culture, infection, protein purification, molecular biology methods and the like are common methods used in the art. Such techniques can be found in reference manuals such as, for example, Sambrook et al. (2001, Molecular Cloning—A Laboratory Manual, Cold Spring Harbor Laboratory Press); Ausubel et al. (1994, Current Protocols in Molecular Biology, Wiley, New York) and Coligan et al. (1995, Current Protocols in Protein Science, Volume 1, John Wiley & Sons, Inc., New York).

The designations "P3, P2, P1, P1', etc." as used herein refer to the position of the amino acid residues starting from the N-terminus of the peptide analogs and extending towards and beyond the cleavage site, i.e. the bond in a substrate of the protease enzyme which is normally cleaved by the catalytic action of the protease enzyme. Thus, P3 refers to position 3 from the C-terminal side of the cleavage site, P2 to position 2 from the C-terminal side of the cleavage site, etc. The bond between the P1 and P1' residues corresponds to the cleavage site. Thus, the P1' position corresponds to the first position on the N-terminal side of the cleavage site (see Berger A. & Schechter I., Transactions of the Royal Society London series B257, 249-264 (1970)). For example, such peptides may be expressed as: P3-P2-P1↓P1'-P2' . . . etc.

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission (Biochemistry, 1972,11:1726-1732).

All values and concentrations presented herein are subject to inherent variations acceptable in biological science within an error of ±10%. The term "about" also refers to this acceptable variation.

The term "negative control" as used herein means a reaction vessel submitted to the same conditions as the others used for the experiment, but with the crucial factor (such as the enzyme or substrate) omitted. In the particular case at hand, the activating agent allowing NS2/3 to self-cleave is omitted in the negative control wells.

NS2/3 Protease

The term "NS2/3", "NS2/3 protein" or "NS2/3 protease", used herein interchangeably, refer to the region of the Hepatitis C Virus (HCV) polyprotein that catalyzes the cleavage of the NS2 domain (810-1026) from the NS3 domain (1027-1615), as well as functionally equivalent variants thereof. In one embodiment as described herein, it is encoded by the native NS2 region (specifically, amino acids 810 to 1026) and the minimal NS3 protease domain (1027 to 1206) of the polyprotein (numbered according to genotype 1a H77 sequence, GenBank accession number AAB67036) herein referred to as 810*-1206 [SEQ ID NO.1; *where amino acid 810 corresponds to amino acid 1 of SEQ ID NO.1].

Functionally equivalent variants of the NS2/3 protease are encompassed by the term "NS2/3", "NS2/3 protein" or "NS2/3 protease", "functionally equivalent" referring to variants able to catalyze the cleavage of NS2/3 such as variants from other HCV isolates/genotypes. The term "variant" also refers to a protein derived from native NS2/3, but modified in sequence by insertion, deletion, substitution, or modification of one or more amino acids. With respect to amino acid substitutions, these will generally include conservative amino acid substitutions that do not affect the NS2/3 function of the protein as would be appreciated by one of skill in the art. It also includes modified amino acids, for example, amino acids including modified side chains.

Furthermore, a "functionally equivalent variant" refers to truncations comprising the minimal catalytic region of the NS2/3 protease that has been determined to comprise the C-terminus of NS2 (beginning at about amino acid position 907 of the polyprotein) and the N-terminus of NS3 (up to amino acid position 1206) (5). Accordingly, NS2/3 truncations comprising these amino acid deletions, termed "NS2/3 fragment" are examples of variants in accordance with the present invention, such as: (907-1206; SEQ ID NO. 2) or (904-1206; SEQ ID NO. 3). Additionally, NS2/3 deletion mutants comprising any number of amino acid deletions between the native sequence of NS2/3 (810-1615 or 810-1206) and truncated NS2/3 (907-1206) are also contemplated to be variants in accordance with the present invention. Other variants are likewise known in the art, such as those described in WO 01/68818, WO 02/48375 and U.S. Pat. No. 6,815,159.

As is well recognized within the skill or the art, the term "variant" also encompasses modifications to the protein such as adding affinity tags or detectable labels in order to facilitate extraction/purification or detection/measurement. Also, substitutions or insertions, such as addition of amino acid(s) to enhance solubility (such as lysine), are also encompassed with the term "variant". One example of such variant is (4K-6H-904-1206-ST-4K) [SEQ ID NO. 4].

If a NS2/3 protease functionally equivalent variant is used in the assay in accordance with the present invention, it is necessary to confirm that the modified peptide retains NS2/3 autocleavage activity. This can be done using standard cleavage assays such as those described in references 2-5, cited herein.

The term "at least a portion of NS2/3 protease is cleaved" means that at least a portion of the total amount of the NS2/3 protease present in the assay mixture is cleaved.

Affinity Tag

The term "affinity label" or "affinity tag", as used herein, means a ligand whose strong affinity for a receptor (or a complementary ligand) can be used to extract (e.g. from a solution) or specifically trap the entity to which the ligand is covalently attached. Affinity tags are indispensable tools that were developed to facilitate the detection and purification of recombinant proteins. They can be classified in two categories: 1) affinity tags that use peptide or protein fusions which bind to small molecule ligands linked to a solid support (hexahistidine tag binding to immobilized transition metals such as nickel, or GST binding to glutathione); or 2) peptide tags binding to an immobilized protein-binding partner (including antibodies) such as the FLAG-tag, the calmodulin-binding peptide, the Strep-tag or Strep-tag II and the biotin acceptor peptide. Examples of pairs of affinity tag/affinity ligand include but are not limited to: Maltose-Binding Protein (MBP)/maltose; Glutathione S Transferase (GST)/glutathione; histidine (His)/metal; avidin/biotin; Strep tag/streptavidin or neutravidin. The metal used as affinity ligand may be selected from the group consisting of: cobalt, zinc, copper, iron, and nickel. The affinity label may be positioned on the N- or C-terminal end of the protein, but particularly on the N-terminus of the protein. Particularly, the metal selected is nickel. The affinity ligand can be set up in columns to facilitate separation by affinity chromatography. For reference, a review paper was recently published (13).

NS3 Protease

As used herein, the term "NS3 protease product" refers to NS3 protease domain that is cleaved or released from the NS2/3 protease. NS3 product may correspond with native NS3 (1027-1615), or may be a functionally equivalent variant thereof, i.e. a variant that retains NS3 protease activity. In one embodiment in a construct described herein, NS3 protease domain is represented by amino acids 1027-1206 of SEQ ID NO.3; however, one of skill in the art will appreciate that NS3 protease product in accordance with the present invention may be modified by insertion, deletion, modification, substitution of one or more amino acids as described above. It is anticipated that such modifications will correspond with modifications existing in the NS3 domain of the NS2/3 protease utilized in the assay. The term "NS3 protease product" is interchangeably used herein with the terms "NS3 product", "NS3 protease" or "cleaved NS3 product".

In the present embodiment, following cleavage of NS2/3 to generate an NS3 protease product, the sample is incubated with a labeled NS3 protease-substrate (also referred to NS3-substrate) in the presence of a sufficient amount of NS4A cofactor and a suitable detergent.

NS3-Substrate

In vitro characterization of synthetic substrates of the NS3 protease based on all the natural cleavage sites revealed the following consensus sequence (D/E)XXXXC↓(A/S) [SEQ ID NO.5] for all trans cleavage sites (14), with X being any amino acid and the scissile bond being located between the P1 residue Cys and the P1' residue Ala or Ser. These studies also showed that the best substrates were based either on the NS4A/NS4B or NS5A/NS5B natural cleavage sites, such as for example: DEMEEC-ASH [SEQ ID NO.6] or DDIVCC-SMSYTW [SEQ ID NO.7] respectively.

The substrate used in the NS2/3 protease assay based on NS3 protease activity has been described in (7). Such depsipeptide substrates incorporate an ester bond between residues P1 and P1' and are efficiently cleaved by serine protease because formation of the acyl-enzyme intermediate is accomplished much more readily due to the more thermodynamically favorable trans-esterification reaction.

Other useful substrates of this invention are those linked to a detectable label. In further embodiments, the NS3-substrate is labeled for detection purposes. The substrate may be labeled using labels conventionally used in the art including, for example, fluorescent labels such as pairs of fluorescent donor radical and fluorescent acceptor radical, other types of detectable labels and colorimetric labels. Other practical and useful detectable labels are radioactive labels such as $^{125}$I, or β-galactosidase. Such other detectable labels may be found in the Invitrogen—Molecular Probes Handbook—*A Guide to Fluorescent Probes and Labeling Technology*, $10^{th}$ ed. 2005.

As used herein, the terms "label", "detectable label" or "detectable marker" refer to any group that may be linked to the NS3 substrate to allow recognition either directly or indirectly of the resulting NS3-substrate byproduct such that it can be detected, measured and quantified. Examples of such "labels" include, but are not limited to, fluorescent labels, chemiluminescent labels, colorimetric labels, enzymatic markers, radioactive isotopes and affinity tags such as biotin. Such labels are attached to the peptide by well known methods. A label, or multiple labels, of the present invention can be introduced at any position on the peptide, for example, the label can be at either the C- or N-terminus or within the peptide so long as it does not disturb its functional properties of being recognized and cleaved by the NS3 protease.

Internally quenched depsipeptide fluorogenic NS3 protease substrates were designed based on resonance energy transfer between a donor/acceptor couple and can be described generically as follows: (donor/acceptor)—P-site amino acid sequence—[C(O)—O]—P'-site amino acid sequence—(acceptor/donor).

The term "fluorescent donor radical", as used herein, means a fluorescence emitting radical which can be modified and attached to the amino acid sequence. Examples of such radicals are those derived from 2-aminobenzoyl (and halogenated derivatives thereof), 5-{(2-aminoethyl)amino}-naphthalene-1-sulfonyl (EDANS), 7-methoxycoumarin-4-acetyl, nicotinic acid (and derivatives thereof) and tryptophan.

The term "fluorescent acceptor radical", as used herein, means an aromatic quenching radical which absorbs the fluorescence energy of the fluorescence donor radical and reduces the fluorescence emission when the fluorescence donor radical is covalently attached in close proximity to the acceptor radical. Examples of such radicals include 3-nitrotyrosine, 4-nitrophenylalanine, 2,4-dinitrophenylalanine, 5-(dimethylamino)naphthalene-1-sulfonyl (DANSYL), 4-{{4-(dimethylamino) phenyl}azo}benzoyl (DABCYL) or 4-(dimethylamino)azobenzene-4'-sulfonyl (DABSYL).

Examples of donor/acceptor radical pair are selected from the following pairs:
EDANS/DABCYL;
tryptophan/2,4-dinitrophenylalanine;
tryptophan/DANSYL;
7-methoxycoumarin-4-acetyl/2,4-dinitrophenylalanine;
2-aminobenzoyl/2,4-dinitrophenylalanine; or
2-aminobenzoyl/3-nitrotyrosine.

NS4A Cofactor

Generally, the NS4A cofactor (also referred to as $NS4A_{peptide}$) is a peptide derived from the central hydrophobic domain of the NS4A protein such as GSVVIVGRIILSGR [SEQ ID NO.8] as described in reference (11). It is to be understood that within the context of the present invention, variants of the NS4A wild type cofactor may be employed in the present invention, such as variants containing conservative substitutions or amino acids added for solubility, so long as the cofactor activity in conjunction with NS3 protease is not compromised. Cofactor activity may be assessed by the method of Urbani et al. (12).

As used herein, the term "detergent" means an amphipathic, surface active molecule with polar and non-polar domains. They bind strongly to hydrophobic molecules or molecular domains to confer water solubility. Examples of detergents include, but are not limited to: sodium dodecyl sulphate (SDS), fatty acid salts, the Triton® family, octyl glycoside, 3-[(3-cholamidopropyl)dimethyl-ammonio]-1-propanesulfonate (CHAPS), sodium dodecyl maltoside (DM), lauryldiethylamine oxide (LDAO), NP-40 and the Tween® family.

As used herein, the term "inhibit", when used in reference to the NS2/3 protease, is intended to mean that the protease's ability to autocleave is decreased. Drugs or ligands that can inhibit NS2/3 protease (hereinafter referred to as potential "inhibitors") may be useful for modulating HCV infection in a population of cells and, therefore, may be useful as medicaments for treating a pathology characterized by the presence of HCV in the cells.

The term "NS3 byproduct", "NS3 protease byproduct" or "NS3 cleavage byproduct" or "NS3 substrate byproduct" used herein interchangeably, mean the product resulting from the cleavage of the NS3 substrate by the NS3 protease whether in the form of NS2/3 or NS3 protease or any other form of active NS3 protease.

Specific Embodiments

Therefore, in one embodiment of the first aspect of the present invention, there is provided a method of detecting NS2/3 autocleavage activity in a sample containing NS2/3 protease, the method comprising the steps of:
 a) subjecting the sample to conditions under which at least a portion of the NS2/3 protease is self-cleaved to yield a NS3 protease product;
 b) incubating the sample containing the NS3 protease product produced in step a) with a suitable amount of a NS4A cofactor in the presence of LDAO or DM and an appropriate NS3-substrate under conditions to permit the NS3 protease product to catalyze cleavage of the NS3-substrate to produce a NS3-substrate byproduct thereof; and
 c) detecting the NS3-substrate byproduct generated in step b), whereby the detection of NS3-substrate byproduct indicates NS2/3 autocleavage activity in the sample.

In one embodiment of the second aspect of the present invention, there is provided an assay for screening a candidate compound for NS2/3 autocleavage inhibitory activity in a sample containing NS2/3 protease, the assay comprising:
 a) subjecting a first sample comprising NS2/3 protease, to conditions under which at least a portion of the NS2/3 protease is self-cleaved to yield a NS3 protease product;
 b) subjecting a second sample comprising NS2/3 protease, in the presence of a candidate compound under the same conditions as those in step a);
 c) incubating each of the first and second samples with a sufficient amount of a NS4A cofactor, in the presence of LDAO or DM and an appropriate NS3-substrate for a period of time sufficient to permit the NS3 protease product to catalyze cleavage of the NS3-substrate, thereby generating a NS3-substrate byproduct;
 d) determining the amount of NS3-substrate byproduct generated in each of the first and second samples, whereby a decrease in amount of NS3-substrate byproduct generated in the second sample as compared with the amount of NS3-substrate byproduct generated in the first sample indicates that the candidate compound may be an inhibitor of NS2/3 autocleavage activity.

Of course, as will be recognized by persons of skill in the art, an appropriate counter-assay must be performed to ensure that one can distinguish between an inhibitor of NS3 protease and an inhibitor of NS2/3 auto-cleavage activity. A counter-assay such as the NS3 protease assay is well known in the art.

NS2/3 Protease Variant

Particularly, NS2/3 variant (4K-6H-904-1206-ST-4K) of SEQ ID NO. 4 is used in the assay of the present invention.

NS2/3 Autocleavage Assay Conditions

In a first step of the present method, a sample is subjected to conditions under which NS2/3 is cleaved to yield a NS3 product. Such conditions, including the use of a detergent as an activation agent, are known in the art (2-5) and suitable conditions are also exemplified herein.

Particularly, the NS2/3 is originally prepared in solution of LDAO to prevent self-cleavage prior to the start of the assay. Particularly, the concentration of LDAO should be well above critical micelle concentration (CMC) in order to block autocleavage. More particularly, in the present assay conditions, LDAO should be present between 0.5 and 1.5% in the solution, most particularly, at about 1%. The NS2/3 solution is afterwards diluted in a solution lacking LDAO, to achieve lower concentrations in order for autocleavage to proceed.

The autocleavage reaction is therefore induced by decreasing the concentration of LDAO, in the presence of an activation agent, the activation agent being a detergent selected from the group consisting of: CHAPS, Triton X-100, NP-40 and n-dodecyl-β-D-maltoside (DM). Typically, the detergent acting as activation agent is present above its CMC.

Typically, glycerol is present to enhance autocleavage, particularly from 0% to 50%, more particularly, from 20% to 50%.

NS3 Protease Assay Conditions

It is to be understood that a range of concentrations may be employed that afford cleavage of the labeled NS3-substrate in conjunction with the NS3 product. In one embodiment, about 1000-fold molar excess of the NS4A cofactor is used relative to the NS3 protease product. In another embodiment, 100-fold molar excess may be utilized. Concentrations useful in the present invention would be understood to be determinable by artisans skilled in the field.

Detergents suitable for use in this step of the present embodiment include those that afford in the presence of NS4A cofactor under suitable conditions, enhanced activity of the protease activity of the NS3 protease towards an NS3-substrate relative to the protease activity of uncleaved NS2/3 towards the same NS3-substrate. In one embodiment, the detergent comprises lauryldiethylamine oxide (LDAO) or n-dodecyl-β-D-maltoside (DM) above their respective critical micelle concentration. In a particular embodiment, the detergent is LDAO at a concentration from 0.2% to 2%; particularly at from 0.5% to 1%, specifically at about 0.5%. Alternatively, the detergent is DM at a concentration from 0.05% to 2%, particularly from 0.2% to 1%, specifically at about 0.2%.

NS4A Cofactor

In one embodiment, the NS4A cofactor is the peptide having the sequence KKGSVVIVGRIILSGRK [SEQ ID NO.9], wherein lysine residues have been added to confer enhanced solubility to the NS4A cofactor.

Labeling of NS3-Substrate

In one embodiment, the substrate is a depsipeptide based on the NS4A/4B cleavage site. More particularly, in a further embodiment, the labeled substrate is the internally-quenched fluorogenic depsipeptide substrate: Ac-DED(EDANS)EE-Abu-[C(O)—O]ASK(DABCYL)-NH$_2$ [SEQ ID NO.10].

Composition of the NS3 Protease Activity Buffer

Typical range for the NS3 protease components are: pH: 6-9; glycerol: 20%-50%; detergent: above its critical micelle concentration; reducing agent: TCEP, dithiothreitol (DTT) or β-mercaptoethanol.

Particularly, the assay buffer composition is as follows: 50 mM HEPES, pH 7.5, 30% glycerol, 0.5% LDAO, 1 mM TCEP containing 4 µM of the fluorogenic substrate Ac-DED(EDANS)EE-Abu[C(O)—O]ASK(DABCYL)-NH$_2$ and 10 µM NS4A$_{peptide}$.

Reaction Conditions

The period of time sufficient to permit NS3 product to catalyze cleavage of a labeled NS3-substrate will be understood to vary depending upon the various conditions employed in the assay. In one embodiment, the time is about 45 minutes.

Once the cleaved reaction mixture is incubated with an NS3-substrate for a sufficient period of time, for example 0.25 to 3.0 hours, although this time could be longer, the amount of NS3 in the sample can be determined based on the amount of labeled byproduct of the NS3 labeled substrate that is generated. This determination will vary with the nature of the label on the NS3-substrate, as one of skill in the art would appreciate, and involves utilization of conventional detection methods.

It is to be understood in the present embodiment and in the various other embodiments disclosed and claimed herein that the general conditions, including buffers employed, pH of buffers and solutions employed, temperatures employed and time of reaction would include those that do not inhibit the intended various steps and would be readily determinable by persons skilled in the art.

Embodiments of the invention are described by reference to the following specific examples which are not to be construed as limiting:

EXAMPLES

Abbreviations

Abu: amino butyric acid;
BSA: Bovine serum albumin;
CHAPS: 3-[(3-cholamidopropyl)dimethyl-ammonio]-1-propanesulfonate;
DABCYL: 4-{{4-(dimethylamino)phenyl}azo}benzoyl
DANSYL: 5-(dimethylamino)naphthalene-1-sulfonyl;
DMSO: dimethyl sulfoxide;
DM: n-dodecyl-β-D-maltoside;
EDANS: 5-{(2-aminoethyl)amino}-naphthalene-1-sulfonyl;
HEPES: 4-(2-hydroxyethyl)-1-piperazineethanesulfonic acid;
LDAO: lauryldiethylamine oxide;
TCEP: Tris(2-carboxyethyl)phosphine hydrochloride.

Materials and Methods

Assay Reagents

BSA, glycerol, HEPES and DMSO were purchased from Sigma-Aldrich. The detergents n-dodecyl-β-D-maltoside (DM) and lauryldiethylamine oxide (LDAO) were from Anathrace Inc. and Fluka respectively. TCEP was from Pierce, Tween®20 from Bio-Rad and sodium chloride from EM Science.

The NS4A-derived cofactor peptide KKGSVVIVGRIILS-GRK (SEQ ID NO.9) was synthesized in-house by using standard solid-phase methodology (6). The internally quenched depsipeptide fluorogenic substrate Ac-DED(EDANS)EE-Abu[C(O)—O]ASK(DABCYL)-NH$_2$ (SEQ ID NO.10) was designed based on the NS4A/4B cleavage site and synthesized according to the method previously described (7).

NS2/3 Protease Preparation

The expression, production and purification of the NS2/3 protease was done according to the procedure previously reported (2). Practically speaking, aliquots of the refolded, inactive NS2/3 protein can be stored frozen at −80° C., and later thawed and diluted to induce autocleavage.

NS3 Protease Preparation

The expression, production and purification of the NS3 protease domain were done according to the procedure previously reported (8).

Example 1

NS2/3 Protease Autocleavage

Activation of the refolded NS2/3 protease requires the use of detergents at concentrations above their critical micelle concentration, although some detergents do not promote autocleavage. Also, the effect of the detergent on NS2/3 autocleavage activity is enhanced in the presence of glycerol (2). The concentration dependence of the NS2/3 protease autocleavage reaction previously reported (4) is confirmed using SDS-PAGE/Western blot analysis. At concentrations greater than 200 nM, no concentration dependence is observed (data not shown). The effect of glycerol, pH and DMSO on autocleavage is also evaluated. Similar cleavage kinetics is observed in a buffer containing 20% or 30% glycerol (data not shown). Finally, autocleavage is optimal at pH 7.5 and DMSO has no effect on activity at concentrations ranging from 0.5-5% (data not shown).

Therefore, the autocleavage reaction is initiated by adding 10 μL of NS2/3 protease (SEQ ID NO.4) at 800 nM in 50 mM HEPES, pH 7.5, 20% glycerol, 1 mM TCEP to 30 μL of 50 mM HEPES, pH 7.5, 20% glycerol, 0.266% n-dodecyl-β-D-maltoside, 1 mM TCEP with the final DMSO content kept at 5%. The reaction mixture is incubated for 45 minutes at room temperature.

In the negative control wells, autocleavage is prevented by adding no activating agent (i.e. DM in this case).

Example 2

NS2/3 Protease Assay Based on NS3 Protease Activity

Kinetic Parameters

Kinetic parameters for the NS3 protease activity of the NS2/3 protease (SEQ ID NO.4) are compared to those of the NS3 protease domain and determined with the fluorogenic substrate Ac-DED(EDANS)EE-Abu[C(O)—O]ASK(DABCYL)-NH$_2$ (SEQ ID NO.10). Substrate cleavage is continuously monitored at room temperature on a BMG POLARstar Galaxy fluorometer, equipped with excitation and emission filters of 355 nm and 485 nm, respectively, in the presence of 0.5 to 8 μM substrate. The NS3 protease activity of the NS2/3 protease (15 to 350 nM) and of the NS3 protease domain (1.5 to 800 nM) is assayed with and without a 1000-fold molar excess of the NS4A$_{peptide}$ in 50 mM HEPES, pH 7.5, 30% glycerol, 5% DMSO, 1 mM TCEP containing 0, 0.5 or 1% LDAO. In the presence of the NS4A$_{peptide}$, a 15-min pre-incubation is introduced to allow for the formation of the protease-cofactor complex.

The catalytic efficiencies of the NS3 protease and of the NS3 protease activity of NS2/3 are comparable in the absence of detergent and of the NS4A$_{peptide}$ cofactor as shown in Table 1. Addition of the zwitterionic detergent LDAO to the assay buffer is detrimental to the protease activity, with catalytic efficiencies decreasing up to 21- and 36-fold for the NS3 protease activity of NS2/3 and for the NS3 protease, respectively (Table 1).

Figure 2:
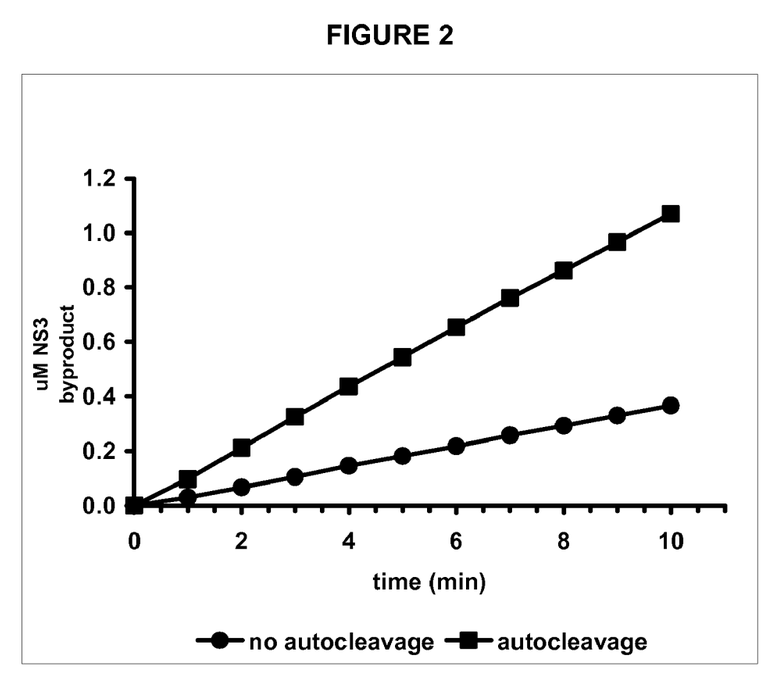
FIG. 2 graphically illustrates NS3 protease activity in an assay sample before and after the step of autocleavage in accordance with the assay of FIG. 1.

The NS3 protease activity of both enzymes is also comparable upon addition of the NS4A cofactor ($6.7 \times 10^4$ M$^{-1}$s$^{-1}$ for NS2/3 and $7.8 \times 10^4$ M$^{-1}$s$^{-1}$ for NS3). Interestingly, addition of the detergent LDAO to the assay buffer containing the NS4A$_{peptide}$ results in an increase in activity for NS3 protease (2.2-fold with 0.5% LDAO and 3.2-fold with 1% LDAO) but has little if any effect on the NS3 protease activity of NS2/3 (Table 1 and FIG. 2). Overall, an up to 3-fold difference in protease activities is observed upon the addition of LDAO to the NS4A$_{peptide}$ containing buffer. This difference in activity allows for the discrimination of the NS3 protease activity between the NS2/3 protease precursor and the NS3 protease product. Consequently, NS2/3 autocleavage can be monitored without separating the precursor and the product. Hence, the NS2/3 protease assay based on NS3 protease activity is initiated with a 20-fold dilution of the autocleavage reaction mixture in a buffer containing the substrate, the NS4A$_{peptide}$ and LDAO. The dilution also contributes to stop autocleavage by 1) decreasing the NS2/3 protease concentration, 2) by inhibition with the NS4A$_{peptide}$ (9, 10) and 3) addition of LDAO.

TABLE 1

Kinetic parameters for the NS3 protease activity of the NS2/3 protease (SEQ ID NO. 4) and of the NS3 protease domain with and without the detergent LDAO and the NS4A$_{peptide}$ co-factor[1].

| Conditions | | NS2/3 protease | | | NS3 protease | | |
| --- | --- | --- | --- | --- | --- | --- | --- |
| LDAO (%) | NS4A | K$_m$ (μM) | k$_{cat}$ (min$^{-1}$) | k$_{cat}$/K$_m$ ($10^4$ M$^{-1}$s$^{-1}$) | K$_m$ (μM) | k$_{cat}$ (min$^{-1}$) | k$_{cat}$/K$_m$ ($10^4$ M$^{-1}$s$^{-1}$) |
| 0 | – | 0.45 | 0.54 | 2.00 | 1.24 | 0.72 | 0.97 |
| 0.5 | – | 2.73 | 0.25 | 0.15 | 5.95 | 0.15 | 0.042 |
| 1 | – | 3.85 | 0.22 | 0.095 | 5.39 | 0.087 | 0.027 |
| 0 | + | 0.57 | 2.30 | 6.73 | 2.42 | 11.3 | 7.78 |
| 0.5 | + | 1.47 | 7.34 | 8.32 | 0.58 | 6.02 | 17.3 |
| 1 | + | 1.43 | 6.56 | 7.65 | 0.75 | 11.1 | 24.7 |

[1]Kinetic parameters are determined by using the depsipeptide fluorogenic substrate Ac-DED(EDANS)EE-Abu[C(O)-O]ASK(DABCYL)-NH$_2$. Data are averages from two separate determinations.

Finally, the kinetic of autocleavage observed using this assay are in agreement with kinetics determined by SDS-PAGE/Western blot analysis (data not shown).

Figure 1:
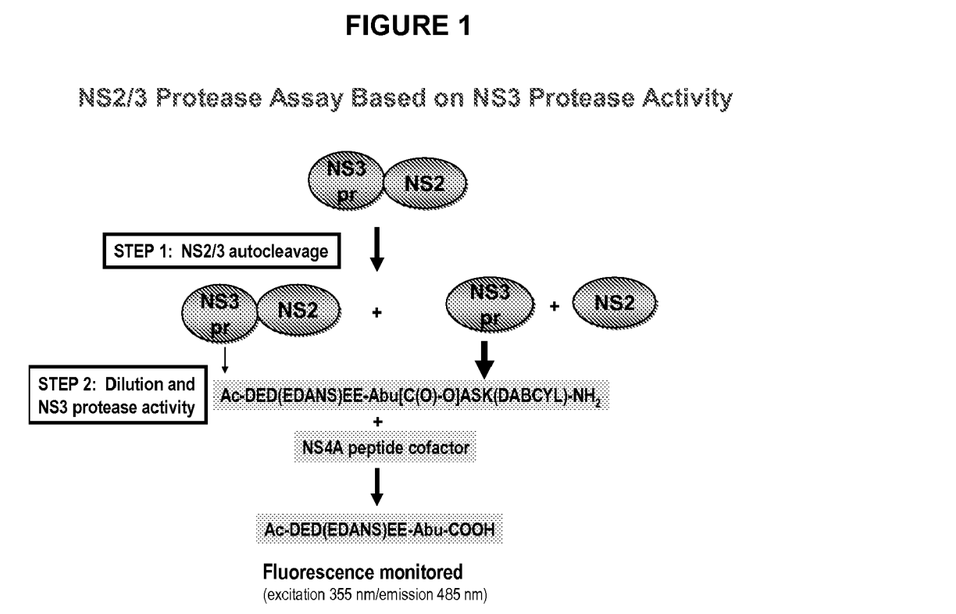
FIG. 1 is a schematic representation of an NS2/3 protease assay in accordance with one aspect of the present invention.

Therefore, 5 µL of the autocleavage reaction mixture is added to 95 µL of 50 mM HEPES, pH 7.5, 30% glycerol, 0.5% LDAO, 1 mM TCEP containing 4 µM of the fluorogenic substrate Ac-DED(EDANS)EE-Abu[C(O)—O]ASK(DAB-CYL)-NH$_2$ and 10 µM NS4A$_{peptide}$. The assay mixture is then incubated for 45 minutes at room temperature. Fluorescence is monitored using the BMG POLARstar® Galaxy set at the appropriate gain with an excitation filter of 355 nm and an emission filter of 485 nm. A schematic representation of the assay is shown in FIG. 1.

Example 3

Assay for Screening Inhibitors

This assay illustrates the kind of format that such an assay may adopt for the purposes of screening a large number of potential inhibitors of HCV NS2/3 protease. As will be apparent from this description, appropriate controls must be run in parallel to evaluate background NS3 protease activity of the uncleaved NS2/3 protein in order to subtract such background activity.

Assay Description

The NS2/3 protease Lys$_4$-His$_6$-[NS2/3 (904-1206)]-strep$_{tag}$-Lys$_4$ [SEQ ID NO.4] is the one used in that assay [enzyme production, purification and refolding are described in (2)]. The autocleavage reaction is performed in a buffer containing n-dodecyl-β-D-maltoside (DM) and glycerol (±test compound) and is initiated by adding the NS2/3 protease followed by a 45-min incubation at room temperature. Assessment of autocleavage is based on monitoring the protease activity of the NS3 protease product. Conditions are found in which the NS3 protease activity of the NS2/3 protease is at least 3-fold lower than the activity of the NS3 protease domain. Consequently, the NS3 protease assay is initiated with a 20-fold dilution of the autocleavage reaction mixture in a buffer containing the NS4A$_{peptide}$ and the NS3 protease substrate. Diluting the NS2/3 protease, adding the NS4A$_{peptide}$ and adding 1% LDAO stop autocleavage.

Ultimately, NS2/3 protease autocleavage results in an increase in fluorescence.

Protocol

A) Autocleavage Reaction

In a 96-well round-bottom polypropylene plate (Falcon) are added:
  30 µL test compound (originally in 100% DMSO but diluted in 50 mM HEPES, pH 7.5, 20% glycerol, 0.266% DM,1 mM TCEP);
  10 µL NS2/3 protease (800 nM in 50 mM HEPES, pH 7.5, 20% glycerol, 1 mM TCEP for a final concentration of 200 nM). The final DMSO content is kept at 5%.

The plate is incubated for 45 min at room temperature.

In the negative control wells, no activating detergent (i.e. DM) is added. In the positive control wells, no test compound is added (in place, a buffer/DMSO solution is added).

B) NS3 Protease Activity

In a 96-well Microfluor white U-bottom plate (Thermo Labsystems) are added:
  95 µL of 50 mM HEPES, pH 7.5, 30% glycerol, 0.5% LDAO, 1 mM TCEP containing 4 µM of NS3 protease fluorogenic substrate (Ac-DED(EDANS)EE-Abu[C(O)—O]ASK(DABCYL)-NH$_2$) [SEQ ID NO.10] and
  10 µM NS4A peptide (NH$_2$-KKGSVVIVGRIILS-GRK—COOH) [SEQ ID NO.9]; and
  5 µL autocleavage mixture from step A).

The wells are incubated for 45 min at room temperature.

Increased fluorescence of the NS3-substrate byproduct [Ac-DED(EDANS)EE-Abu-COOH] is monitored using a BMG POLARstar Galaxy or a TECAN GENios Pro plate reader set at the appropriate gain with an excitation filter of 355 nm and an emission filter of 485 nm.

Figure 3:
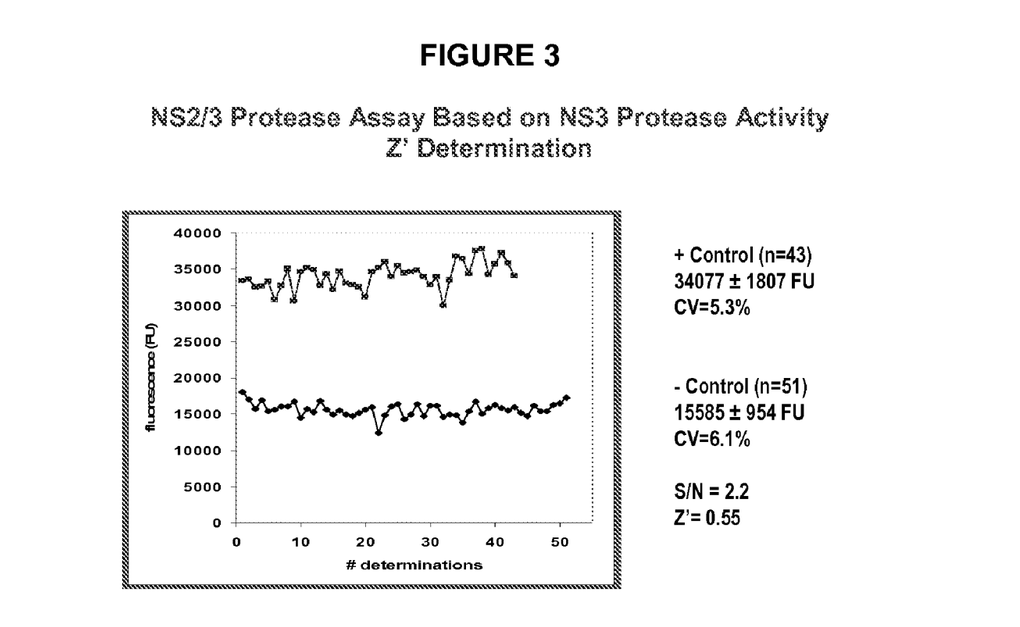
FIG. 3 graphically illustrates the results obtained with an NS2/3 protease assay in accordance with the assay of Example 3.

Results of this experiment are presented in FIG. 3 where it can be seen that the signal window of 2.2 is stable between the positive control (maximal NS3 protease activity of cleaved NS3 protease) and the negative control (background NS3 protease activity of uncleaved NS2/3 protein) with a Z' of 0.55 [Z' being a statistical parameter defined in (15)].

Figure 4:
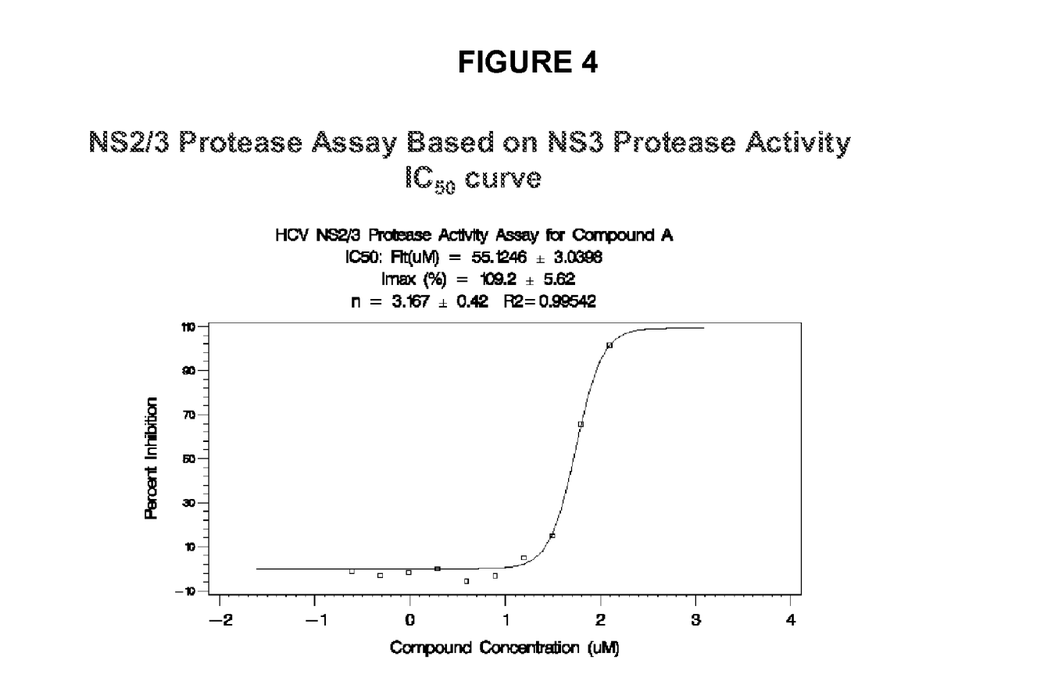
FIG. 4 graphically illustrates the IC$_{50}$ curve of compound A obtained with an embodiment of the present NS2/3 protease assay in accordance with Example 3.

FIG. 4 shows the results obtained with the same assay on test compound A diluted at different concentrations. The % inhibition is calculated with the following equation:

$$100-[(f.u.^{inh}-f.u.^{-ctl})/(f.u.^{+ctl}-f.u.^{-ctl})\times 100].$$

(f.u.: fluorescence units; inh: test compound; −ctl: negative control; +ctl: positive control)

A non-linear curve fit with the Hill model is applied to the inhibition-concentration data, and the 50% effective concentration (IC$_{50}$) is calculated by the use of SAS software (Statistical Software System; SAS Institute, Inc., Cary, N.C.).

An IC$_{50}$ of approximately 55 µM is obtained for compound A.

Of course, as will be well recognized by a person of skill in the art, an appropriate counter-assay must be performed to ensure that positive results are not "false-positive" caused by an inhibitor of NS3 protease. To eliminate such "false-positive" test compounds, appropriate "shadow plates" are set up as step B (NS3 protease activity) of the NS2/3 assay but the NS2/3 protease is replaced with NS3 protease.

Alternatively, each positive compound may be counter-screened later in an appropriate NS3 protease assay as is well know in the art (14).

In conclusion, in the NS2/3 protease assay based on NS3 protease activity presented herein, the protease activity of the NS3 product is directly measured following dilution of the autocleavage mixture in a buffer containing the substrate, the NS4A$_{peptide}$ cofactor and the detergent LDAO or DM that allow the discrimination of the NS3 protease activity of the NS2/3 protease precursor and of the NS3 protease product. Consequently, no separation step is required.

REFERENCES (1) Kolykhalov, A. A., Mihalik, K., Feinstone, S. M. and C. M. Rice. (2000) Hepatitis C virus-encoded enzymatic activities and conserved RNA elements in the 3'-nontranslated region are essential for virus replication in vivo. *J. Virol.* 74: 2046-2051.

(2) Thibeault, D., Maurice, R., Pilote, L., Lamarre, D. and Pause, A. (2001) In vitro characterization of a purified NS2/3 protease variant of hepatitis C virus. *J. Biol. Chem.* 276 (49): 46678-46684.

(3) Boehringer Ingelheim (Canada) Ltd. U.S. Pat. No. 6,815,159 (9 Nov. 2004) Purified active HCV NS2/3 protease.

(4) Pallaoro, M., Lahm, A., Biasiol, G., Brunetti, M., Nardella, C., Orsatti, L., Bonelli, F., Orrù, S, Narjes, F. and Steinkühler, C. (2001) Characterization of the hepatitis C virus NS2/3 processing reaction by using a purified precursor protein. *J. Virol.* 75: 9939-9946.

(5) Istituto di ricerche di biologia molecolare P. Angeletti, Italy. Patent application WO 01/68818 A2 (priority 17 Mar. 2000), HCV NS2/3 fragments and uses thereof.
(6) Bodansky, M. (1993) Peptide Chemistry, $2^{nd}$ edition, Springer-Verlag, Berlin.
(7) Bianchi, E., Steinkühler, C., Taliani, M., Urbani, A., De Francesco, R., and A. Pessi. (1996) Synthetic depsipeptide substrates for the assay of human hepatitis C virus protease. *Analyt. Biochem.* 237: 239-244.
(8) LaPlante, S. R., Cameron, D. R., Aubry, N., Lefebvre, S., Kukolj, G., Maurice, R., Thibeault, D., Lamarre, D., and Llinas-Brunet, M. (1999) Solution structure of substrate-based ligands when bound to hepatitis C virus NS3 protease domain. *J. Biol. Chem.* 274 (26), 18618-18624.
(9) Darke, P. L., Jacobs, A. R., Waxman, L., and L. C. Kuo (1999) Inhibition of hepatitis C virus NS2/3 processing by NS4A peptides. *J. Biol. Chem.* 274: 34511-34514.
(10) Merck & Co., Patent application WO 02/16379 A1 (priority 30 Aug. 1999), Hepatitis C virus replication inhibitors.
(11) Lin, C., Thomson, J. A. and C. M. Rice. 1995. A central region in the hepatitis C virus NS4A protein allows formation of an active NS3-NS4A serine proteinase complex in vivo and in vitro. *J. Virol.* 69: 4373-4380.
(12) Urbani, A., Biasiol, G., Brunetti, M., Volpari, C., Di Marco, S., Sollazzo, M., Orrù, S., Dal Piaz, F., Casbarra, A., Pucci, P., Nardi, C., Gallinari, P., De Francesco, R., and Steinkühler, C. (1999) Multiple determinants influence complex formation of the hepatitis C virus NS3 protease domain with its NS4A cofactor peptide. *Biochemistry* 38 (16): 5206-5215.
(13) Waugh, D. S. 2005; Making the most of affinity tags; Trends Biotechnology 23: 316-320.
(14) Steinkühler C., Urbani A., Tomei L., Biasiol G., Mohinder S., Bianchi E., Pessi A., DeFrancesco R. (1996) Activity of Purified Hepatitis C virus Protease NS3 on Peptide Substrates, *J. Virol.* 70(10): 6694-6700.
(15) Zhang J.-H., Chung, T. D. Y., Oldenburg K. R. (1999) A Simple Statistical Parameter for Use in Evaluation and Validation of High Throughput Screening, *J. of Biomol. Screening* 4(2): 67-73.

The invention claimed is:

1. A rapid screening method for detecting NS2/3 autocleavage activity in a sample containing uncleaved NS2/3 protease and cleaved NS3 protease product, the method comprising the steps of:
   a) subjecting the sample to conditions under which at least a portion of the NS2/3 protease is self-cleaved to yield a NS3 protease product and said sample comprising uncleaved NS2/3 protease and said cleaved NS3 protease product;
   b) incubating the sample containing the NS3 protease product generated in step a) with a suitable amount of a NS4A cofactor in the presence of a detergent selected from the group consisting of lauryldiethylamine oxide (LDAO) and n-dodecyl-13-D-maltoside (DM), and an appropriate NS3-substrate under conditions sufficient to permit the NS3 protease product to catalyze cleavage of the NS3-substrate to produce an NS3-substrate byproduct thereof, said detergent discriminating in situ the protease activity of the uncleaved NS2/3 protease from the protease activity of the cleaved NS3 protease product; and
   c) detecting the NS3-substrate byproduct generated in step b), whereby the detection of NS3-substrate byproduct indicates NS2/3 autocleavage activity in the sample.

2. The method according to claim 1, wherein LDAO at a concentration from 0.2% to 2%.

3. The method according to claim 1, wherein DM at a concentration from 0.05% to 2%.

4. The method according to claim 1, wherein said NS2/3 protease comprises the polypeptide of SEQ ID NO:11.

5. The method according to claim 4, wherein said NS2/3 protease comprises the polypeptide of SEQ ID NO:2.

6. The method according to claim 4, wherein said NS2/3 protease comprises the polypeptide of SEQ ID NO:3.

7. The method according to claim 4, wherein said NS2/3 protease further comprises an affinity tag or a detectable label.

8. The method according to claim 7, wherein said NS2/3 protease comprises the polypeptide of SEQ ID NO:4.

9. The method according to claim 1, wherein said NS4A cofactor comprises a peptide having the sequence of SEQ ID NO:8.

10. The method according to claim 9, wherein said NS4A cofactor has the sequence of SEQ ID NO:9.

11. The method according to claim 9, wherein said NS4A cofactor is used at 1000-fold molar excess relative to the NS3 protease product.

12. The method according to claim 1, wherein said NS3 substrate is based on a consensus sequence comprising the sequence (D or E)XXXXC(A or S) wherein X is any amino acid.

13. The method according to claim 12, wherein said NS3 substrate comprises a depsipeptide selected from the group consisting of: SEQ ID NO:6 and SEQ ID NO:7.

14. The method according to claim 12, wherein said NS3 substrate comprises SEQ ID NO:10.

* * * * *

SEQUENCE LISTING

<160> NUMBER OF SEQ ID NOS: 11

<210> SEQ ID NO 1
<211> LENGTH: 1191
<212> TYPE: DNA
<213> ORGANISM: HCV

<400> SEQUENCE: 1

| | | | | | | | | | | | | | | | | |
|---|---|---|---|---|---|---|---|---|---|---|---|---|---|---|---|---|
| atg | gac | cgg | gag | atg | gct | gca | tcg | tgc | gga | ggc | gcg | gtt | ttc | ata | ggt | 48 |
| ctt | gca | ctc | ttg | acc | ttg | tca | cca | tac | tat | aaa | gtg | ctc | ctc | gct | agg | 96 |
| ctc | ata | tgg | tgg | tta | cag | tat | tta | atc | acc | aga | gtc | gag | gcg | cac | ttg | 144 |
| caa | gtg | tgg | atc | ccc | cct | ctc | aat | gtt | cgg | gga | ggc | cgc | gat | gcc | atc | 192 |
| atc | ctc | ctc | acg | tgc | gca | gtc | cac | cca | gag | cta | atc | ttt | gac | atc | acc | 240 |
| aaa | ctc | ctg | ctc | gcc | ata | ttc | ggt | ccg | ctc | atg | gtg | ctc | cag | gca | ggc | 288 |
| ata | acc | aaa | gtg | ccg | tac | ttc | gtg | cgt | gcg | cag | ggg | ctc | att | cgt | gcg | 336 |
| tgt | atg | ttg | gtg | cgg | aag | gct | gcg | ggg | ggt | cat | tat | gtc | caa | atg | gcc | 384 |
| ttc | atg | aag | cta | gct | gcg | ctg | aca | ggt | acg | tac | gtt | tat | gac | cat | ctc | 432 |
| act | cca | ttg | cag | gat | tgg | gcc | cac | gcg | ggc | cta | cga | gac | ctt | gca | gtg | 480 |
| gcg | gta | gag | ccc | gtc | atc | ttc | tct | gac | atg | gag | gtc | aag | atc | atc | acc | 528 |
| tgg | ggg | gcg | gac | acc | gcg | gca | tgc | ggg | gac | atc | att | tca | ggt | ctg | ccc | 576 |
| gtc | tcc | gct | cga | agg | gga | agg | gag | ata | ctc | ctg | gga | ccg | gcc | gat | aat | 624 |
| ttt | gaa | ggg | cag | ggg | tgg | cga | ctc | ctt | gcg | ccc | atc | acg | gcc | tac | tcc | 672 |
| caa | cag | aca | cgg | ggc | cta | ctt | ggt | tgc | atc | atc | acc | agc | ctc | aca | ggc | 720 |
| cgg | gac | aag | aac | cag | gtc | gag | ggg | gag | gtt | caa | gtg | gtc | tcc | acc | gct | 768 |
| aca | caa | tct | ttc | ctg | gcg | acc | tgc | gtc | aac | ggc | gtg | tgt | tgg | act | gtc | 816 |
| ttc | cat | ggc | gcc | ggc | tca | aag | acc | ttg | gcc | ggc | ccc | aaa | ggc | cca | atc | 864 |
| acc | cag | atg | tac | act | aat | gtg | gac | cag | gac | ctc | gtc | ggc | tgg | cag | gcg | 912 |
| ccc | cct | ggg | gcg | cgc | tcc | atg | aca | cca | tgc | acc | tgc | ggc | agc | tcg | gac | 960 |

-continued

```
ctc tat ttg gtc acg aga cat gcc gac gtc att ccg gtg cgc cgg cgg    1008 ggc gac agt agg ggg agc ctg ctc tcc ccc agg cct gtc tcc tac ttg    1056 aag ggc tct tcg ggt ggc cca ctg ctc tgc cct tcg ggg cac gtt gtg    1104 ggc atc ttc cgg gct gct gtg tgc acc cgg ggg gtt gca aaa gcg gtg    1152 gac ttc ata cct gtt gag tct atg gaa act acc atg cgg                1191
```

<210> SEQ ID NO 2
<211> LENGTH: 300
<212> TYPE: PRT
<213> ORGANISM: HCV

<400> SEQUENCE: 2

```
Thr Lys Val Pro Tyr Phe Val Arg Ala Gln Gly Leu Ile Arg Ala Cys
 1               5                  10                  15

Met Leu Val Arg Lys Ala Ala Gly Gly His Tyr Val Gln Met Ala Phe
            20                  25                  30

Met Lys Leu Ala Ala Leu Thr Gly Thr Tyr Val Tyr Asp His Leu Thr
        35                  40                  45

Pro Leu Gln Asp Trp Ala His Ala Gly Leu Arg Asp Leu Ala Val Ala
    50                  55                  60

Val Glu Pro Val Ile Phe Ser Asp Met Glu Val Lys Ile Ile Thr Trp
65                  70                  75                  80

Gly Ala Asp Thr Ala Ala Cys Gly Asp Ile Ile Ser Gly Leu Pro Val
                85                  90                  95

Ser Ala Arg Arg Gly Arg Glu Ile Leu Leu Gly Pro Ala Asp Asn Phe
            100                 105                 110

Glu Gly Gln Gly Trp Arg Leu Leu Ala Pro Ile Thr Ala Tyr Ser Gln
        115                 120                 125

Gln Thr Arg Gly Leu Leu Gly Cys Ile Ile Thr Ser Leu Thr Gly Arg
    130                 135                 140

Asp Lys Asn Gln Val Glu Gly Glu Val Gln Val Val Ser Thr Ala Thr
145                 150                 155                 160

Gln Ser Phe Leu Ala Thr Cys Val Asn Gly Val Cys Trp Thr Val Phe
                165                 170                 175

His Gly Ala Gly Ser Lys Thr Leu Ala Gly Pro Lys Gly Pro Ile Thr
            180                 185                 190

Gln Met Tyr Thr Asn Val Asp Gln Asp Leu Val Gly Trp Gln Ala Pro
        195                 200                 205

Pro Gly Ala Arg Ser Met Thr Pro Cys Thr Cys Gly Ser Ser Asp Leu
    210                 215                 220

Tyr Leu Val Thr Arg His Ala Asp Val Ile Pro Val Arg Arg Arg Gly
225                 230                 235                 240

Asp Ser Arg Gly Ser Leu Leu Ser Pro Arg Pro Val Ser Tyr Leu Lys
                245                 250                 255

Gly Ser Ser Gly Gly Pro Leu Leu Cys Pro Ser Gly His Val Val Gly
            260                 265                 270

Ile Phe Arg Ala Ala Val Cys Thr Arg Gly Val Ala Lys Ala Val Asp
        275                 280                 285

Phe Ile Pro Val Glu Ser Met Glu Thr Thr Met Arg
    290                 295                 300
```

<210> SEQ ID NO 3
<211> LENGTH: 303
<212> TYPE: PRT

<213> ORGANISM: HCV

<400> SEQUENCE: 3

Ala Gly Ile Thr Lys Val Pro Tyr Phe Val Arg Ala Gln Gly Leu Ile
1               5                   10                  15

Arg Ala Cys Met Leu Val Arg Lys Ala Ala Gly Gly His Tyr Val Gln
            20                  25                  30

Met Ala Phe Met Lys Leu Ala Ala Leu Thr Gly Thr Tyr Val Tyr Asp
        35                  40                  45

His Leu Thr Pro Leu Gln Asp Trp Ala His Ala Gly Leu Arg Asp Leu
    50                  55                  60

Ala Val Ala Val Glu Pro Val Ile Phe Ser Asp Met Glu Val Lys Ile
65                  70                  75                  80

Ile Thr Trp Gly Ala Asp Thr Ala Ala Cys Gly Asp Ile Ile Ser Gly
                85                  90                  95

Leu Pro Val Ser Ala Arg Arg Gly Arg Glu Ile Leu Leu Gly Pro Ala
            100                 105                 110

Asp Asn Phe Glu Gly Gln Gly Trp Arg Leu Leu Ala Pro Ile Thr Ala
        115                 120                 125

Tyr Ser Gln Gln Thr Arg Gly Leu Leu Gly Cys Ile Ile Thr Ser Leu
    130                 135                 140

Thr Gly Arg Asp Lys Asn Gln Val Glu Gly Glu Val Gln Val Val Ser
145                 150                 155                 160

Thr Ala Thr Gln Ser Phe Leu Ala Thr Cys Val Asn Gly Val Cys Trp
                165                 170                 175

Thr Val Phe His Gly Ala Gly Ser Lys Thr Leu Ala Gly Pro Lys Gly
            180                 185                 190

Pro Ile Thr Gln Met Tyr Thr Asn Val Asp Gln Asp Leu Val Gly Trp
        195                 200                 205

Gln Ala Pro Pro Gly Ala Arg Ser Met Thr Pro Cys Thr Cys Gly Ser
    210                 215                 220

Ser Asp Leu Tyr Leu Val Thr Arg His Ala Asp Val Ile Pro Val Arg
225                 230                 235                 240

Arg Arg Gly Asp Ser Arg Gly Ser Leu Leu Ser Pro Arg Pro Val Ser
                245                 250                 255

Tyr Leu Lys Gly Ser Ser Gly Gly Pro Leu Leu Cys Pro Ser Gly His
            260                 265                 270

Val Val Gly Ile Phe Arg Ala Ala Val Cys Thr Arg Gly Val Ala Lys
        275                 280                 285

Ala Val Asp Phe Ile Pro Val Glu Ser Met Glu Thr Thr Met Arg
    290                 295                 300

<210> SEQ ID NO 4
<211> LENGTH: 334
<212> TYPE: PRT
<213> ORGANISM: HCV

<400> SEQUENCE: 4

Met Lys Lys Lys Lys Leu Glu His His His His His Thr Ser Ala
1               5                   10                  15

Gly Ile Thr Lys Val Pro Tyr Phe Val Arg Ala Gln Gly Leu Ile Arg
            20                  25                  30

Ala Cys Met Leu Val Arg Lys Ala Ala Gly Gly His Tyr Val Gln Met
        35                  40                  45

Ala Phe Met Lys Leu Ala Ala Leu Thr Gly Thr Tyr Val Tyr Asp His

-continued

```
                50                  55                  60
Leu Thr Pro Leu Gln Asp Trp Ala His Ala Gly Leu Arg Asp Leu Ala
 65                  70                  75                  80

Val Ala Val Glu Pro Val Ile Phe Ser Asp Met Glu Val Lys Ile Ile
                 85                  90                  95

Thr Trp Gly Ala Asp Thr Ala Ala Cys Gly Asp Ile Ile Ser Gly Leu
                100                 105                 110

Pro Val Ser Ala Arg Arg Gly Arg Glu Ile Leu Leu Gly Pro Ala Asp
                115                 120                 125

Asn Phe Glu Gly Gln Gly Trp Arg Leu Leu Ala Pro Ile Thr Ala Tyr
130                 135                 140

Ser Gln Gln Thr Arg Gly Leu Leu Gly Cys Ile Ile Thr Ser Leu Thr
145                 150                 155                 160

Gly Arg Asp Lys Asn Gln Val Glu Gly Glu Val Gln Val Val Ser Thr
                165                 170                 175

Ala Thr Gln Ser Phe Leu Ala Thr Cys Val Asn Gly Val Cys Trp Thr
                180                 185                 190

Val Phe His Gly Ala Gly Ser Lys Thr Leu Ala Gly Pro Lys Gly Pro
                195                 200                 205

Ile Thr Gln Met Tyr Thr Asn Val Asp Gln Asp Leu Val Gly Trp Gln
                210                 215                 220

Ala Pro Pro Gly Ala Arg Ser Met Thr Pro Cys Thr Cys Gly Ser Ser
225                 230                 235                 240

Asp Leu Tyr Leu Val Thr Arg His Ala Asp Val Ile Pro Val Arg Arg
                245                 250                 255

Arg Gly Asp Ser Arg Gly Ser Leu Leu Ser Pro Arg Pro Val Ser Tyr
                260                 265                 270

Leu Lys Gly Ser Ser Gly Gly Pro Leu Leu Cys Pro Ser Gly His Val
                275                 280                 285

Val Gly Ile Phe Arg Ala Ala Val Cys Thr Arg Gly Val Ala Lys Ala
                290                 295                 300

Val Asp Phe Ile Pro Val Glu Ser Met Glu Thr Thr Met Arg Thr Ser
305                 310                 315                 320

Ser Ala Trp Arg His Pro Gln Phe Gly Gly Lys Lys Lys Lys
                325                 330
```

<210> SEQ ID NO 5
<211> LENGTH: 7
<212> TYPE: PRT
<213> ORGANISM: HCV
<220> FEATURE:
<221> NAME/KEY: VARIANT
<222> LOCATION: (1)...(1)
<223> OTHER INFORMATION: Xaa at position 1 can be ASP or Glu
<221> NAME/KEY: VARIANT
<222> LOCATION: (2)...(2)
<223> OTHER INFORMATION: Xaa at position 2 can be any amino acid
<221> NAME/KEY: VARIANT
<222> LOCATION: (3)...(3)
<223> OTHER INFORMATION: Xaa at position 3 can be any amino acid
<221> NAME/KEY: VARIANT
<222> LOCATION: (4)...(4)
<223> OTHER INFORMATION: Xaa at position 4 can be any amino acid
<221> NAME/KEY: VARIANT
<222> LOCATION: (5)...(5)
<223> OTHER INFORMATION: Xaa at position 5 can be any amino acid
<221> NAME/KEY: VARIANT
<222> LOCATION: (7)...(7)
<223> OTHER INFORMATION: Xaa at position 7 can be Ala or Ser

<400> SEQUENCE: 5

```
Xaa Xaa Xaa Xaa Xaa Cys Xaa
 1               5

<210> SEQ ID NO 6
<211> LENGTH: 9
<212> TYPE: PRT
<213> ORGANISM: HCV

<400> SEQUENCE: 6

Asp Glu Met Glu Glu Cys Ala Ser His
 1               5

<210> SEQ ID NO 7
<211> LENGTH: 12
<212> TYPE: PRT
<213> ORGANISM: HCV

<400> SEQUENCE: 7

Asp Asp Ile Val Cys Cys Ser Met Ser Tyr Thr Trp
 1               5                  10

<210> SEQ ID NO 8
<211> LENGTH: 14
<212> TYPE: PRT
<213> ORGANISM: HCV

<400> SEQUENCE: 8

Gly Ser Val Val Ile Val Gly Arg Ile Ile Leu Ser Gly Arg
 1               5                  10

<210> SEQ ID NO 9
<211> LENGTH: 17
<212> TYPE: PRT
<213> ORGANISM: HCV

<400> SEQUENCE: 9

Lys Lys Gly Ser Val Val Ile Val Gly Arg Ile Ile Leu Ser Gly Arg
 1               5                  10                  15
Lys

<210> SEQ ID NO 10
<211> LENGTH: 9
<212> TYPE: PRT
<213> ORGANISM: HCV
<220> FEATURE:
<221> NAME/KEY: VARIANT
<222> LOCATION: (1)...(1)
<223> OTHER INFORMATION: Asp at position 1 is capped with Acetyl
<221> NAME/KEY: VARIANT
<222> LOCATION: (3)...(3)
<223> OTHER INFORMATION: Asp at position 3 is tagged with EDANS
<221> NAME/KEY: VARIANT
<222> LOCATION: (6)...(6)
<223> OTHER INFORMATION: Xaa at position 6 is Abu[C(O)-O]
<221> NAME/KEY: VARIANT
<222> LOCATION: (9)...(9)
<223> OTHER INFORMATION: Lys at position 9 is tagged with DABCYL

<400> SEQUENCE: 10

Asp Glu Asp Glu Glu Xaa Ala Ser Lys
 1               5

<210> SEQ ID NO 11
<211> LENGTH: 397
<212> TYPE: PRT
<213> ORGANISM: HCV
```

<400> SEQUENCE: 11

Met Asp Arg Glu Met Ala Ala Ser Cys Gly Gly Ala Val Phe Ile Gly
1               5                   10                  15

Leu Ala Leu Leu Thr Leu Ser Pro Tyr Tyr Lys Val Leu Leu Ala Arg
            20                  25                  30

Leu Ile Trp Trp Leu Gln Tyr Leu Ile Thr Arg Val Glu Ala His Leu
        35                  40                  45

Gln Val Trp Ile Pro Pro Leu Asn Val Arg Gly Gly Arg Asp Ala Ile
    50                  55                  60

Ile Leu Leu Thr Cys Ala Val His Pro Glu Leu Ile Phe Asp Ile Thr
65                  70                  75                  80

Lys Leu Leu Leu Ala Ile Phe Gly Pro Leu Met Val Leu Gln Ala Gly
                85                  90                  95

Ile Thr Lys Val Pro Tyr Phe Val Arg Ala Gln Gly Leu Ile Arg Ala
            100                 105                 110

Cys Met Leu Val Arg Lys Ala Ala Gly Gly His Tyr Val Gln Met Ala
        115                 120                 125

Phe Met Lys Leu Ala Ala Leu Thr Gly Thr Tyr Val Tyr Asp His Leu
    130                 135                 140

Thr Pro Leu Gln Asp Trp Ala His Ala Gly Leu Arg Asp Leu Ala Val
145                 150                 155                 160

Ala Val Glu Pro Val Ile Phe Ser Asp Met Glu Val Lys Ile Ile Thr
                165                 170                 175

Trp Gly Ala Asp Thr Ala Ala Cys Gly Asp Ile Ile Ser Gly Leu Pro
            180                 185                 190

Val Ser Ala Arg Arg Gly Arg Glu Ile Leu Leu Gly Pro Ala Asp Asn
        195                 200                 205

Phe Glu Gly Gln Gly Trp Arg Leu Leu Ala Pro Ile Thr Ala Tyr Ser
    210                 215                 220

Gln Gln Thr Arg Gly Leu Leu Gly Cys Ile Ile Thr Ser Leu Thr Gly
225                 230                 235                 240

Arg Asp Lys Asn Gln Val Glu Gly Glu Val Gln Val Val Ser Thr Ala
                245                 250                 255

Thr Gln Ser Phe Leu Ala Thr Cys Val Asn Gly Val Cys Trp Thr Val
            260                 265                 270

Phe His Gly Ala Gly Ser Lys Thr Leu Ala Gly Pro Lys Gly Pro Ile
        275                 280                 285

Thr Gln Met Tyr Thr Asn Val Asp Gln Asp Leu Val Gly Trp Gln Ala
    290                 295                 300

Pro Pro Gly Ala Arg Ser Met Thr Pro Cys Thr Cys Gly Ser Ser Asp
305                 310                 315                 320

Leu Tyr Leu Val Thr Arg His Ala Asp Val Ile Pro Val Arg Arg Arg
                325                 330                 335

Gly Asp Ser Arg Gly Ser Leu Leu Ser Pro Arg Pro Val Ser Tyr Leu
            340                 345                 350

Lys Gly Ser Ser Gly Gly Pro Leu Leu Cys Pro Ser Gly His Val Val
        355                 360                 365

Gly Ile Phe Arg Ala Ala Val Cys Thr Arg Gly Val Ala Lys Ala Val
    370                 375                 380

Asp Phe Ile Pro Val Glu Ser Met Glu Thr Thr Met Arg
385                 390                 395